United States Patent [19]

Takagi et al.

[11] Patent Number: 4,932,774
[45] Date of Patent: Jun. 12, 1990

[54] ILLUMINATING SYSTEM OF OPHTHALMOLOGICAL INSTRUMENT

[75] Inventors: Kazutoshi Takagi; Nobuaki Kitajima; Kazuo Nunokawa, all of Tokyo, Japan

[73] Assignee: Tokyo Kogaku Kikai Kabushiki Kaisha, Tokyo, Japan

[21] Appl. No.: 159,948

[22] Filed: Feb. 24, 1988

[30] Foreign Application Priority Data

Feb. 24, 1987 [JP] Japan .................................. 62-39082
Feb. 24, 1987 [JP] Japan .................................. 62-39083

[51] Int. Cl.$^5$ ............................................. A61B 3/10
[52] U.S. Cl. ..................................... 351/221; 351/214
[58] Field of Search ............... 351/205, 206, 212, 214, 351/221

[56] References Cited

U.S. PATENT DOCUMENTS

3,944,343 3/1976 Mueller, Jr. ..................... 351/221
4,265,518 5/1981 Matsumura ..................... 351/221
4,411,502 10/1983 Lang et al. ..................... 351/214

Primary Examiner—P. M. Dzierzynski
Attorney, Agent, or Firm—Finnegan, Henderson, Farabow, Garrett & Dunner

[57] ABSTRACT

An illuminating system of an ophthalmological instrument has a coaxial illuminating system for effecting a coaxial illumination by projecting an observation-use illuminating light toward an eye to be tested from a direction generally parallel with an optical axis of through an objective lens of an observing optical system, FIGS. 1A and 1B each illustrated an oblique illuminating system branched from the coaxial illuminating system and adapted to effect an oblique illumination by projecting the observation-use illuminating light toward the eye from an oblique direction different from the coaxial illumination, and an optical path switching optical member disposed in an intermediate part of an optical path of the coaxial illuminating system and adapted to switch the coaxial illumination to the oblique illumination or vice versa.

9 Claims, 10 Drawing Sheets

ILLUMINATING SYSTEM OF OPHTHALMOLOGICAL INSTRUMENT

BACKGROUND OF THE INVENTION

1. Field of the Invention

This invention relates to an improvement on an illuminating system of an ophthalmological instrument.

2. Prior Art of the Invention

A conventional illuminating system of an ophthalmological instrument such as a microscope for use in operation comprises an observation-use coaxial illuminating system for projecting an observation-use illuminating light from a direction parallel to the optical axis (so-called coaxial direction in a sense that it illuminates through a lens-barrel of an objective lens) of an objective lens of an observating optical system toward an eye to be tested, and an observation-use oblique illuminating system for projecting an observation-use illuminating light from an oblique direction different from the coaxial illumination toward the eye through a slit to effect an oblique direction eye illumination (hereinafter referred to as the "oblique illumination"). In the illuminating system of this conventional ophthalmological instrument, a light source of the observation-use oblique illuminating system and a light source of the observation-use coaxial illuminating system are separately provided, and a switch for switching the light source of the observation-use illuminating system to the light source of the observation-use coaxial illuminating system, or vice versa is located in a position far away from an operator.

However, in this kind of illuminating system of an ophthalmological instrument, because the light source of the observation-use oblique illuminating system and the light source of the observation-use coaxial illuminating system must be separately prepared, a housing for containing the illuminating system of the ophthalmological instrument becomes too large. Therefore, when this is employed in an operation-use microscope, the large housing often becomes an obstacle during operation. Moreover, because the switch for the respective light sources is located in a position far away from the operator, it is difficult for the operator to rapidly switch the oblique illumination over to the coaxial illumination, or vice versa. In order to effect a switch-over operation rapidly, an assistance of a nurse, etc. is necessary and thus inconvenient.

As another prior art, there is known an illuminating system of an ophthalmological instrument which comprises the observation-use coaxial illuminating system and a photographic-use coaxial illuminating system for projecting a stroboscopic light toward an eye to be tested from the same direction to its illuminating direction in order to illuminate the eye.

In this conventional device, there is provided a quick return mirror for switching the optical path of the observation-use coaxial illuminating light to the optical path of the photographic-use stroboscopic light, or vice versa so as to guide the observation-use illuminating light to an objective lens of an observing optical system of a microscope during observation and to guide a stroboscopic light to the objective lens during photographing.

By the way, there is a case in which the eye is preferably illuminated from a direction different from the coaxial direction, i.e., from an oblique direction. In a case like this, if an observation-use oblique illuminating system for effecting an oblique illumination and a photographic-use oblique illuminating system are made as one pair, and if these are separately provided from one pair consisting of an observation-use coaxial illuminating system for effecting a coaxial illumination and a photographic-use illuminating system, an observation-use light source, a stroboscopic light source, a quick mirror for switching optical paths, etc. must be provided separately. This eventually makes the illuminating apparatus of an ophthalmological instrument too large and complicated. In addition to that, the costs become high and thus not preferable.

SUMMARY OF THE INVENTION

It is therefore a first object of the present invention to provide an illuminating system of an ophthalmological instrument, in which an operator can rapidly switch a coaxial illumination to an oblique illumination or vice versa while avoiding a housing for containing the illuminating system of an ophthalmological instrument to become too large.

A second object of the present invention is to provide an illuminating system of an ophthalmological instrument, in which an oblique illumination and a coaxial illumination can be effected not only during observation but also during photographing and, at the same time, the illuminating system of an ophthalmological instrument is avoided to become too large, complicated and cost-up.

A third object of the present invention is to provide an illuminating system of an ophthalmological instrument, in which a coaxial illumination and an oblique illumination can be effected simultaneously by an observation-use illuminating light and/or a photographic-use illuminating light.

The feature of the present invention is that there is provided an oblique illuminating system for illuminating an eye to be tested from an oblique direction, and the oblique illuminating system is jointed to an intermediate part of an optical path of an coaxial use illuminating system, and it includes an optical path switching optical member for switching the coaxial use illuminating optical path to the oblique illuminating system optical path or vice versa.

Another feature of the present invention is that it includes a photographic-use illuminating system for emitting a stroboscopic light during photographing, and the photographic-use illuminating system is connected to an optical path jointing portion of the oblique illuminating system and the coaxial illuminating system as such that an oblique illumination and a coaxial illumination can be effected simultaneously through the optical path of the coaxial illuminating system and the optical path of the oblique illuminating system.

Further feature of the present invention is that the optical path switching optical member has a plane mirror, and the optical path jointing portion has a half mirror.

BRIEF DESCRIPTION OF THE DRAWINGS

FIGS. 5 through 8 are illustrations for explaining a fifth embodiment of an illuminating system of an ophthalmological instrument according to the present invention, wherein;

DETAILED DESCRIPTION OF THE PREFERRED EMBODIMENT

Figure 1A:
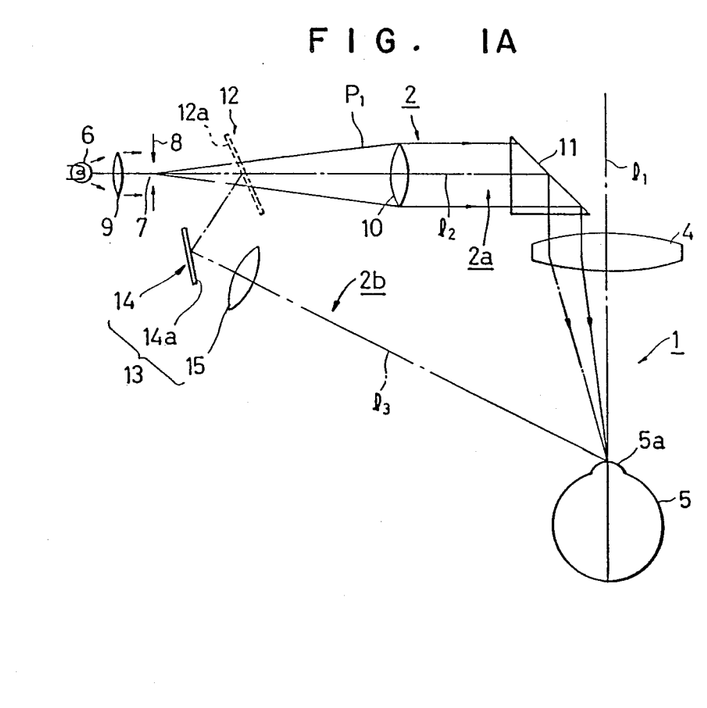
FIGS. 1A and 1B each illustrates an arrangement of an optical system showing a first embodiment of an illuminating system of an ophthalmological instrument according to the present invention.
Figure 1B:
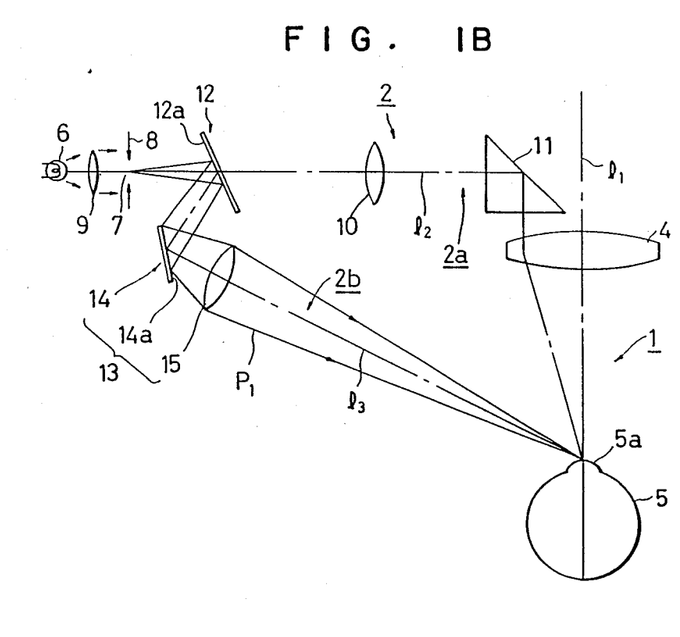

FIGS. 1A and 1B each illustrates a first embodiment of an illuminating system of an ophthalmological instrument according to the present invention. In the figures, reference numeral 1 denotes an observating optical system, and 2 denotes an observation-use illuminating system. Regarding the observating optical system 1, only an objective lens 4 thereof is shown. The objective lens 4 is faced with an eye-to-be-tested (hereinafter simply referred to as the "eye") 5. 1 denotes an optical axis of its objective lens 4.

The observation-use illuminating system 2 comprises a coaxial illuminating system $2a$ and an oblique illuminating system $2b$. The coaxial illuminating system $2a$ generally comprises a light source 6 for emitting an observation-use illuminating light $P_1$, a diaphragm 8 having a slit 7, a condenser lens 9 disposed between the slit diaphragm 8 and the light source 6 and adapted to condense the observation-use illuminating light $P_1$ and to illuminate the slit diaphragm 8, a projecting lens for projecting a slit image on the eye 5 through the objective lens 104, and a reflecting prism 11 for reflecting the observation-use illuminating light $P_2$ passed through the projecting lens 10 toward the objective lens 4. 1 denotes an optical axis of the coaxial illuminating system $2a$. The object point of the projecting lens 10 is located in a position where the slit diaphragm 8 is located.

In an intermediate part of an optical path of the coaxial illuminating system $2a$, a plane mirror 12 as a member for switching an optical path is reciprocally movably disposed with respect to the optical path. The plane mirror 12 is driven by, for example, a solenoid motor. The plane mirror 12 is flipped in and flipped out in a direction vertical to a paper surface here. The plane mirror 12 is formed one surface thereof with a total reflecting surface $12a$. When the plane mirror 12 is retreated from the optical path of the coaxial illuminating system $2a$, as shown in FIG. 1A, the light source 6 is lighted up. Then, the observation-use illuminating light $P_1$ is guided to the objective lens 4 through the objective lens 10 and the prism 11, and a coaxial illumination is effected by the observation-use illuminating light $P_1$.

The slit diaphragm 8 is variable in its slit width and in its slit length. The slit diaphragm 8 is also rotatable about the optical axis $1_2$ within a plane vertical to the optical axis $1_2$. When opened to its full extent, the slit diaphragm 8 is able to uniformly illuminate the eye 5.

And, when the slit diaphragm 8 is rotated about the axis $1_2$ within the plane vertical to the optical axis $1_2$, a slit illumination is rotated in the meridian direction of a cornea $5a$ of the eye 5.

The plane mirror 12 constitutes a part of an oblique illuminating system $2b$ for effecting an oblique illumination by projecting the observation-use illuminating light $P_1$ toward the eye 5 from the oblique direction different from the coaxial illumination. A projecting system 13 of the oblique illuminating system $2b$ includes a plane mirror 14 having a total reflecting surface $14a$ and a projecting lens 15. The oblique illuminating system $2b$ and the coaxial illuminating system $2a$ are contained within a housing (not shown) for containing an illuminating system of an ophthalmological instrument.

The object point of the projecting lens 15 is located in a position where the slit diaphragm 8 is placed, whereas the image point thereof is located in a position where the eye 5 is located. If the light source 6 is lighted up when the plane mirror 12 is advanced into the optical path of the coaxial illuminating system $2a$, as shown in FIG. 1B. The observation-use illuminating light $P_1$ is reflected by the plane mirrors 12 and 14 and guided to the projecting lens 15 so as to effect an oblique illumination. Reference character $1_3$ denotes an optical axis of the oblique illuminating system 13.

In this way, according to the arrangement of the first embodiment, since the observation-use illuminating light $P_1$ is commonly used for the coaxial illumination and an oblique illumination, an operator can rapidly switch the coaxial illumination to the oblique illumination or vice versa without his operation of a switch for the light sources while avoiding the housing for containing the illuminating system of the ophthalmological instrument to become too large.

Figure 2:
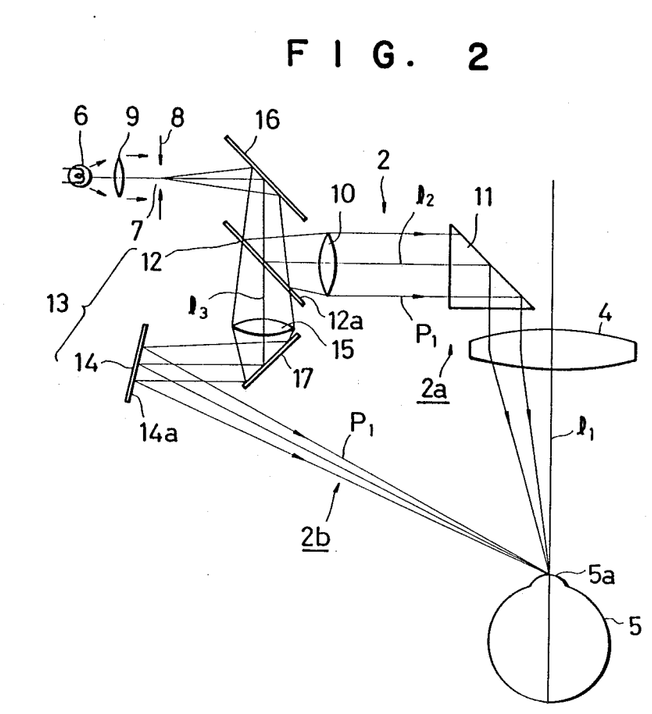
FIG. 2 is an arrangement of an optical system showing a second embodiment of an illuminating system of an ophthalmological instrument according to the present invention.

FIG. 2 illustrates a second embodiment of an illuminating system of an ophthalmological instrument according to the present invention. In the illustrated embodiment, a plane mirror 12 disposed at an intermediate part of an optical path of a coaxial illuminating system $2a$ is tilted by 45° with respect to an optical $1_2$ of the coaxial illuminating system $2a$, and a plane mirror 16 for guiding an observation-use illuminating light $P_1$ passed through a slit diaphragm 8 to the plane mirror 12 is disposed between the plane mirror 12 and the slit diaphragm 8. And, the optical axis $1_2$ of the coaxial illuminating system $2a$ is intersected with an optical axis $1_3$ of an oblique illuminating system $2b$ in a position where the plane mirror 12 is located. Further, a projecting lens 15 is disposed in a position symmetric with a projecting lens 10 by serving the plane mirror 12 as a surface symmetry. Furthermore, there is provided a reflecting mirror 17 for reflecting the observation-use illuminating light passed through the projecting lens 15 toward the plane mirror 14. Still further, the linear distance between the projecting lens 10 and a light source 6 is designed short so as to make the illuminating system of an ophthalmological instrument compact. The remaining constitution is the same as the first embodiment. Therefore, the corresponding parts are denoted by identical reference numerals and the detailed description thereof will be omitted.

Figure 3:
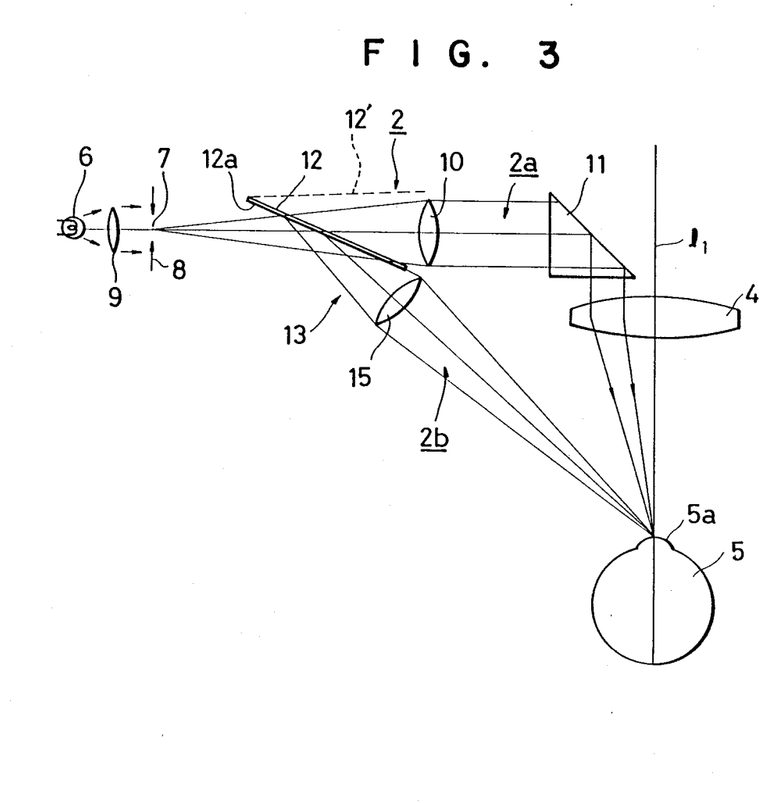
FIG. 3 is an arrangement of an optical system showing a third embodiment of an illuminating system of an ophthalmological instrument according to the present invention.

FIG. 3 illustrates a third embodiment of an illuminating system of an ophthalmological instrument according to the present invention. In this embodiment, the tilting angle of a plane mirror 12 with respect to an optical axis $1_2$ of the coaxial illuminating system $2a$ of the first embodiment is established as such that an oblique illumination can be effected without a provision of a reflecting mirror 14. In this way, the constitution of the oblique illuminating system 26 can be simplified. Further, the plane mirror 12 is able to turn to a position designated by 12'. The remaining constitution is the same as the first embodiment. Therefore, the corresponding component parts are denoted by identical reference numerals and the detailed description thereof will be omitted.

Figure 4:
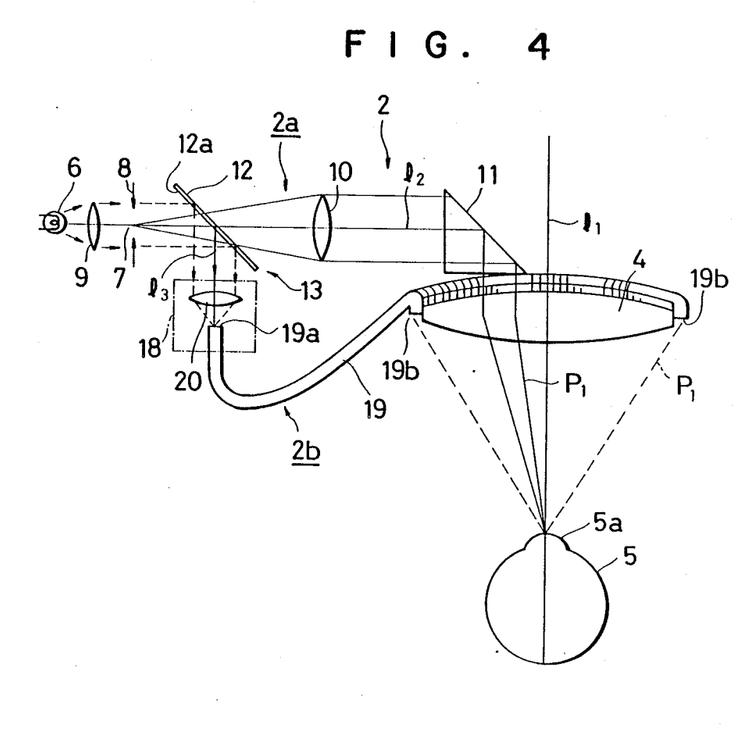
FIG. 4 is an arrangement of an optical system showing a fourth embodiment of an illuminating system according to an ophthalmological instrument.

FIG. 4 illustrates a fourth embodiment of an illuminating system of an ophthalmological instrument according to the present invention. In this embodiment, a mouthpiece 18 is provided to an optical path of an oblique illuminating system 2b so that the connecting portion integrally having an incident end 19a of a light guide 19 for a keratometer adapted to measure the radius of curvature of a cornea and a lens 20 is connectable, whereas the output end 19b thereof is diversified into a plurality of branches which are annularly arranged on the outer peripheral portion of an objective lens 4. By this, a cornea 5a of an eye-to-be-tested 5 can be illuminated with a ring-shaped light pattern when the oblique illuminating is effected. Identical component parts to those of the first embodiment are denoted by identical reference numerals. It is noted that when the ring-shaped illumination is effected, a slit diaphragm 8 is opened to its full extent.

If the projective lens 10 employed in the afore-mentioned embodiments is a zoom type, an illuminating view field is variable during the coaxial illumination.

Figure 5:
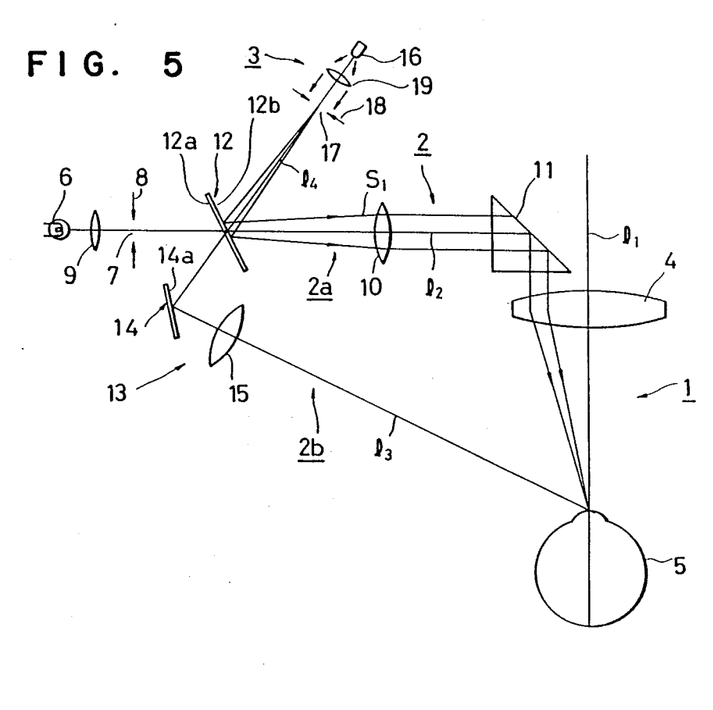
FIG. 5 is a view showing an important optical system thereof.
Figure 6:
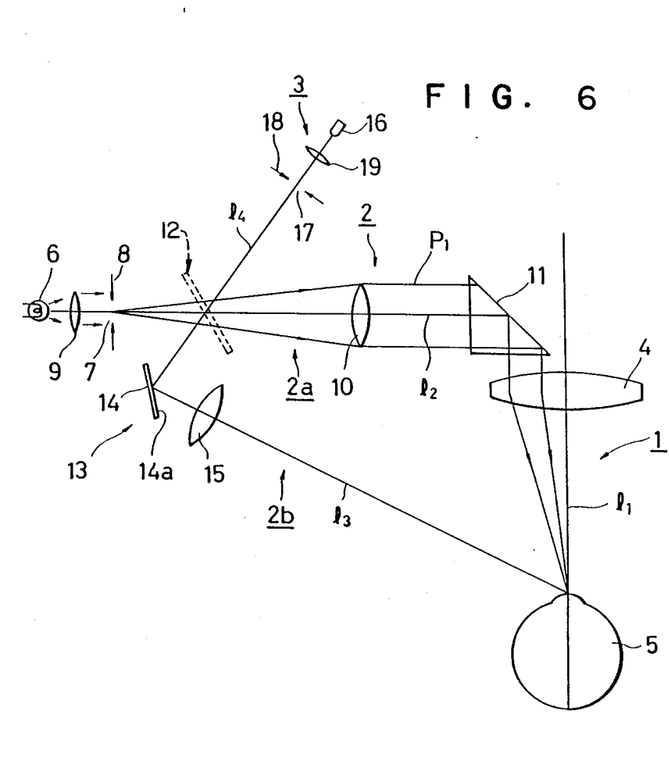
FIGS. 6 through 8 are schematic views for explaining the function thereof.
Figure 7:
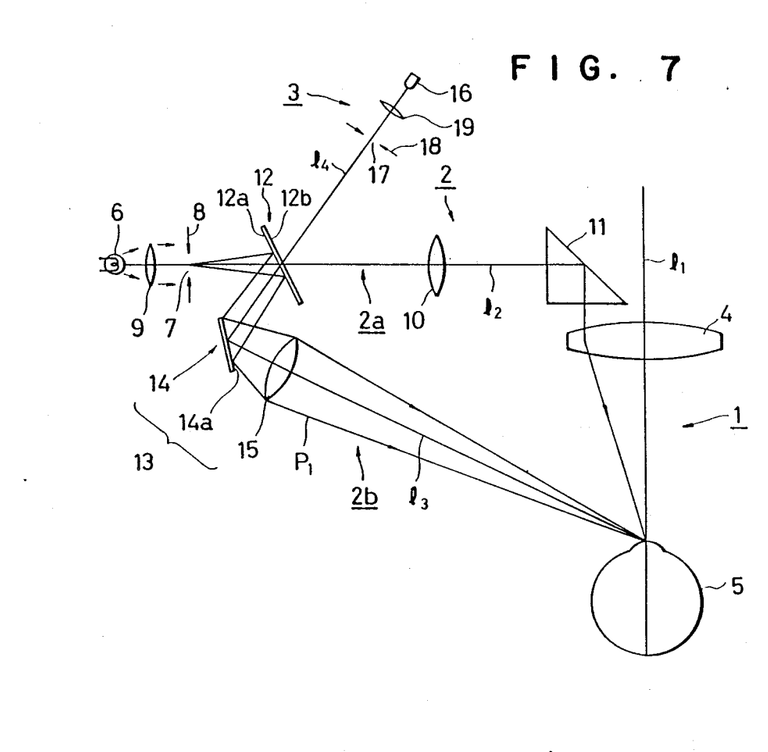
Figure 8:
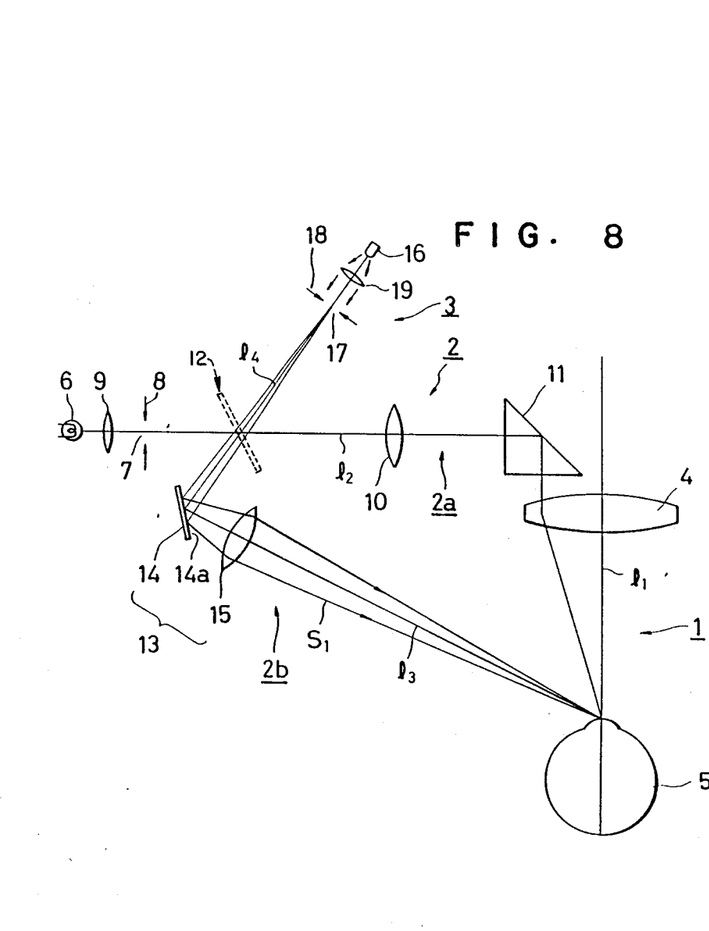

FIGS. 5 through 8 illustrate a fifth embodiment. In this fifth embodiment, reference numeral 3 denotes an photographic-use illuminating system. The photographic-use illuminating system 3 is connected with the obervating optical system 2 of the first embodiment (FIG. 1) through the plane mirror 12. In this embodiment, the plane mirror 12 is formed having surfaces 12a and 12b which are total reflecting surfaces. This photographic-use illuminating system 3 generally comprises a stroboscopic light source 16 for emitting a stroboscopic light $S_1$, a slit diaphragm 18 having a slit 17, and a condenser lens 19 disposed between the slit diaphragm 18 and the stroboscopic light source 16 which is adapted to condense the stroboscopic light $S_1$ so as to illuminate the slit diaphragm 18. The photographic-use illuminating system 3 is disposed so that the coaxial illumination and the oblique illumination of the stroboscopic light $S_1$ can be effected utilizing the oblique illuminating system 2b and the coaxial illuminating system 2a of the observating optical system 2. Reference character $1_4$ denotes an optical axis of the photographic-use illuminating system 3. In this photographic-use illuminating system 3, as shown in FIG. 5, if the stroboscopic light source 16 is lighted up when the plane mirror 12 is advanced to the observation-use illuminating system 2, the stroboscopic light $S_1$ is reflected by the reflecting surface 12b of the plane mirror 12 toward a projecting lens 10, and a coaxial illumination is effected by the stroboscopic light through a prism 11 and an objective lens 4. On the other hand, if the stroboscopic light source 16 is lighted up when the plane mirror 12 is retreated from the optical path of the observation-use illuminating system 2, the stroboscopic light $S_1$, as shown in FIG. 8, is reflected by the plane mirror 14 and guided to the projecting lens 15, and an oblique illumination is effected by the stroboscopic light $S_1$. The coaxial illumination effected by the light source 6 during observation is shown in FIG. 6, whereas the optical path of the oblique illumination is likewise shown in FIG. 7. The illuminating function during the afore-mentioned observation is the same as the first embodiment.

According to this fifth embodiment, it is possible that the plane mirror 12 is retreated from the optical path and the coaxial illumination is effected by the observation-use illumination during observation, as shown in FIG. 6 and thereafter the oblique illumination is effected by the stroboscopic light $S_1$ during photographing as shown in FIG. 8. On the contrary, it is also possible that the plane mirror 12 is advanced into the optical path and the oblique illumination is effected by the observation-use illuminating light $P_1$ during observation, as shown in FIG. 7, and thereafter the coaxial illumination is effected by the stroboscopic light $S_1$ during photographing, as shown in FIG. 5. Further, since the oblique illuminating system 2b, the coaxial illuminating system 2a, and the photographic-use illuminating system 3 are arranged such as shown in FIG. 5, both the oblique illumination and the coaxial illumination can be effected while avoiding the illuminating apparatus of an ophthalmological instrument to become too large, complicated and costly.

Figure 9:
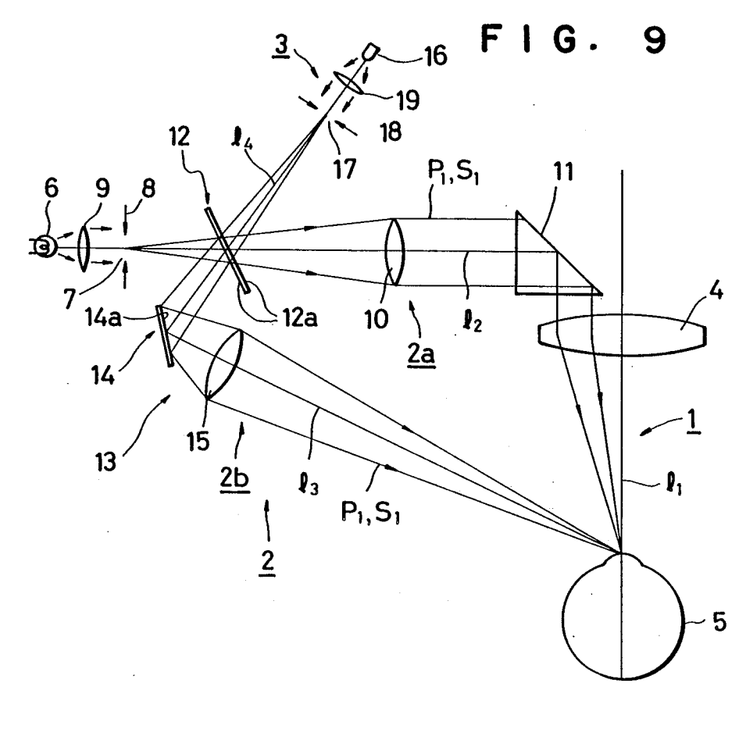
FIG. 9 is an illustration for explaining a sixth embodiment of an illuminating system of an ophthalmological instrument according to the present invention.

FIG. 9 illustrates a sixth embodiment of an illuminating system of an ophthalmological instrument according to the present invention, in which a half mirror is employed as the plane mirror 12. According to this embodiment, when the light source 6 is lighted up, the observation-use illuminating light $P_1$ is reflected by the plane mirror 12 and a part thereof is allowed to pass through the plane mirror 12. Accordingly, the coaxial illumination and the oblique illumination can be simultaneously effected by the observation-use illuminating light $P_1$. Moreover, since a part of the stroboscopic light $S_1$ is also reflected by the plane mirror 12 and a part thereof is allowed to pass through the plane mirror 12 when the stroboscopic light source 16 is lighted up, the coaxial illumination and the oblique illumination can be simultaneously effected by the stroboscopic light $S_1$.

Although the present invention has been described with reference to the preferred embodiments, many modifications and alternations may be made within the spirit of the present invention.

What is claimed is:

1. An illuminating system of an ophthalmological instrument, which includes an observation optical system having an objective lens, comprising:
    a coaxial illuminating system for effecting a coaxial illumination by projecting an observation-use illuminating light toward an eye to be tested from a direction generally parallel with an optical axis of the objective lens of the observation optical system through an objective lens of an observing optical system, said coaxial illuminating system including a zoom type projecting lens for making its view field variable;
    an oblique illuminating system branched from said coaxial illuminating system and adapted to effect an oblique illumination by projecting the observation-use illuminating light toward the eye from an oblique direction different from the coaxial illumination; and
    an optical path switching optical member disposed in an intermediate part of an optical path of said coaxial illuminating system and adapted to selectively switch between the coaxial illumination and the oblique illumination.

2. An illuminating system of an ophthalmological instrument as claimed in claim 1, wherein said oblique illuminating system projects a ring-shaped pattern onto a cornea of the eye.

3. An illuminating system of an ophthalmological instrument as claimed in claim 1, wherein said coaxial illuminating system includes a light source for emitting the observation-use illuminating light and a slit diaphragm disposed in front of said light source, and said slit diaphragm is rotatable about the optical axis of said coaxial illuminating system within a plane vertical to said optical axis.

4. An illuminating system of an ophthalmological instrument comprising
an observation-use illuminating system including a coaxial illuminating system and an oblique illuminating system;
said coaxial illuminating system for projecting an observation-use illuminating light toward an object from a direction generally parallel with an optical axis of an objective lens of an observating optical system through the objective lens;
said oblique illuminating system branched from an optical path of said coaxial illuminating system at a branch point and adapted to project the observation-use illuminating light toward the object from an oblique direction different from that of the coaxial illumination;
a photographic-use illuminating system for emitting a photographing light during photographing; and
optical path jointing means disposed to the branch point so as to join said photographic-use illuminating system with said oblique illuminating system and said coaxial illuminating system; and
whereby both the coaxial illumination and oblique illumination by the photographing light can be effected through at least one of the optical paths of said coaxial illuminating system and said oblique illuminating system of said observation-use illuminating system.

5. An illuminating system of an ophthalmological instrument as claimed in claim 4, wherein said optical path jointing means includes a plane mirror with both surfaces thereof formed in reflecting surfaces, said plane mirror is reciprocally movable with respect to the optical path of said observation-use illuminating system, said optical path jointing means being advanced into said optical path when the oblique illumination by the observation-use illuminating light and the coaxial illumination by the photographing light are effected, whereas said optical path jointing means being retreated from said optical path when the coaxial illumination by the observation-use illuminating light and the oblique illumination by the photographing light are effected.

6. An illuminating system of an ophthalmological instrument as claimed in claim 4, wherein said optical path jointing means is a half mirror.

7. An illuminating system of an observation microscope, which includes an observation system having an objective lens, comprising:
a housing containing a coaxial illumination system, an oblique illumination system and at least the objective lens of the observation system;
said coaxial illumination system including
a light source which emits an observation-use illumination light,
a slit diaphragm disposed in front of said light source and rotatable about an optical axis of said coaxial illumination system within a plane vertical to the optical axis,
first reflection means disposed between the objective lens of the observation system and the light source, said first reflection means reflecting the light emitted from said light source along a direction parallel to an optical axis of the objective lens, and
first projection lens disposed between said slit diaphragm and said first reflection means and which projects the light emitted through said slit diaphragm toward an eye to be treated through both said first reflection means and the objective lens; and
said oblique illumination system including
second reflection means disposed obliquely about an optical axis of said coaxial illumination system between said slit diaphragm and said first projection lens of said coaxial illumination system and which is able to be retreated from and advanced into an optical path of said coaxial illumination system, and
second projection lens for projecting the light reflected from said second reflection means toward the eye along an oblique direction different from the coaxial direction.

8. An illuminating system of an ophthalmological instrument, which includes an observation optical system having an objective lens, comprising:
a coaxial illumination system for effecting a coaxial illumination by projecting an observation-use illuminating light toward an eye to be tested from a direction generally parallel with an optical axis of the objective lens of the observation optical system through the objective lens;
an oblique illumination system branched from said coaxial illumination system and adapted to effect an oblique illumination by projection of a ring-shaped pattern onto a cornea of the eye from an oblique direction different from the coaxial illumination for measuring a radius of curvature of the cornea in cooperation with a keratometer; and
an optical path switching optical member disposed in an intermediate part of an optical path of said coaxial illumination system and adapted to selectively switch between the coaxial illumination and the oblique illumination.

9. An illuminating system as claimed in claim 8, wherein said oblique illumination system includes an optical fiber having an output end which is annular in shape and disposed around the objective lens of the observation optical system.

* * * * *

UNITED STATES PATENT AND TRADEMARK OFFICE
CERTIFICATE OF CORRECTION

PATENT NO. : 4,932,774

DATED : June 12, 1990

INVENTOR(S) : Kazutoshi TAKAGI et al.

It is certified that error appears in the above-identified patent and that said Letters Patent is hereby corrected as shown below:

TITLE PAGE:

In the abstract, line 6, delete "through";
     line 7, ",Figs. 1A and 1B
each illustrated" is changed to --through
the objective lens,--.

Column 7, line 21 "observating" is changed to
--observation".

Signed and Sealed this

Second Day of July, 1991

Attest:

HARRY F. MANBECK, JR.

Attesting Officer    Commissioner of Patents and Trademarks